(12) United States Patent
    Van Appeldoorn et al.

(10) Patent No.: US 9,795,804 B2
(45) Date of Patent: Oct. 24, 2017

(54) AFTERLOADING DEVICE, AND USE THEREOF

(71) Applicant: Nucletron Operations B.V., Veenendaal (NL)

(72) Inventors: Adriaan Van Appeldoorn, Veenendaal (NL); Jeroen Schuurman, Veenendaal (NL); Martin Van Beek, Veenendaal (NL); Finn Sollen, Veenendaal (NL); Johan Henning, Veenendaal (NL); Arie Luite Visscher, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 149 days.

(21) Appl. No.: 14/283,470

(22) Filed: May 21, 2014

(65) Prior Publication Data

US 2014/0350325 A1    Nov. 27, 2014

(30) Foreign Application Priority Data

May 22, 2013    (NL) ..................................... 2010838

(51) Int. Cl.
    *A61N 5/10*    (2006.01)
    *G01T 1/02*    (2006.01)

(52) U.S. Cl.
    CPC ......... *A61N 5/1007* (2013.01); *A61N 5/1048* (2013.01); *G01T 1/02* (2013.01);
    (Continued)

(58) Field of Classification Search
    CPC .. A61N 5/1007; A61N 5/1014–5/1017; A61N 5/1027;
    (Continued)

(56) References Cited

U.S. PATENT DOCUMENTS 6,320,935 B1    11/2001  Shinar et al.
6,458,068 B1    10/2002  Ellard et al.
(Continued)

FOREIGN PATENT DOCUMENTS

DE          4138249 A1    5/1993
DE     102004008373 B3    9/2005
(Continued)

OTHER PUBLICATIONS

Andersen, Claus E. et al., "Time-resolved in vivo luminescence dosimetry for online error detection in pulsed dose-rate brachytherapy," Medical Physics, vol. 36, No. 11, Nov. 2009, 5033-5043 (11 pages).
(Continued)

*Primary Examiner* — Charles A Marmor, II
*Assistant Examiner* — Thaddeus Cox
(74) *Attorney, Agent, or Firm* — Bookoff McAndrews, PLLC

(57) ABSTRACT

An afterloading device for effectuating a brachytherapy treatment, comprising a first elongated flexible transport element, arranged to maneuver a radiation source between a storage position inside the afterloading device and a treatment position outside the afterloading device, the afterloading device further comprising a second elongated flexible transport element, having at least one transducer, the second transport element being arranged to move the at least one transducer between a first transducer position and a second transducer position.

20 Claims, 5 Drawing Sheets

(52) U.S. Cl.
CPC .......... *A61N 5/1049* (2013.01); *A61N 5/1064* (2013.01); *A61N 5/1071* (2013.01); *A61N 5/1075* (2013.01); *A61N 2005/1008* (2013.01); *A61N 2005/1024* (2013.01)

(58) Field of Classification Search
CPC ............... A61N 2005/1008–2005/1012; A61N 2005/1018–2005/1025
See application file for complete search history.

(56) References Cited

U.S. PATENT DOCUMENTS

| | | | |
|---|---|---|---|
| 6,553,326 B1* | 4/2003 | Kirsch | A61B 5/06 324/207.17 |
| 6,615,070 B2 | 9/2003 | Lee | |
| 7,107,089 B2 | 9/2006 | Lee | |
| 7,662,083 B2 | 2/2010 | Gueye et al. | |
| 8,133,167 B2 | 3/2012 | Gueye et al. | |
| 8,231,516 B2 | 7/2012 | Maschke | |
| 2003/0163016 A1 | 8/2003 | Testardi | |
| 2003/0212302 A1* | 11/2003 | Rozenfeld | A61N 5/1007 600/1 |
| 2005/0101824 A1* | 5/2005 | Stubbs | A61N 5/1015 600/3 |
| 2006/0014997 A1* | 1/2006 | Kindlein | A61N 5/1015 600/3 |
| 2006/0241332 A1* | 10/2006 | Klein | A61N 5/1015 600/1 |
| 2010/0152521 A1 | 6/2010 | Price | |
| 2010/0288934 A1* | 11/2010 | Keppel | G01T 1/205 250/362 |
| 2013/0204072 A1 | 8/2013 | Verard et al. | |
| 2013/0303902 A1* | 11/2013 | Smith | A61B 6/12 600/431 |
| 2014/0303423 A1* | 10/2014 | Amthor | A61N 5/1027 600/8 |
| 2014/0357977 A1* | 12/2014 | Zhou | A61B 5/061 600/409 |

FOREIGN PATENT DOCUMENTS

| | | |
|---|---|---|
| EP | 1 272 862 | 4/2001 |
| EP | 2543412 A1 | 1/2013 |
| WO | WO 2008/009917 | 1/2008 |
| WO | WO-2012/034157 A1 | 3/2012 |

OTHER PUBLICATIONS

Written Opinion and Search Report issued for Netherlands Application No. NL 2010838, dated Aug. 17, 2013 (11 pages).

* cited by examiner

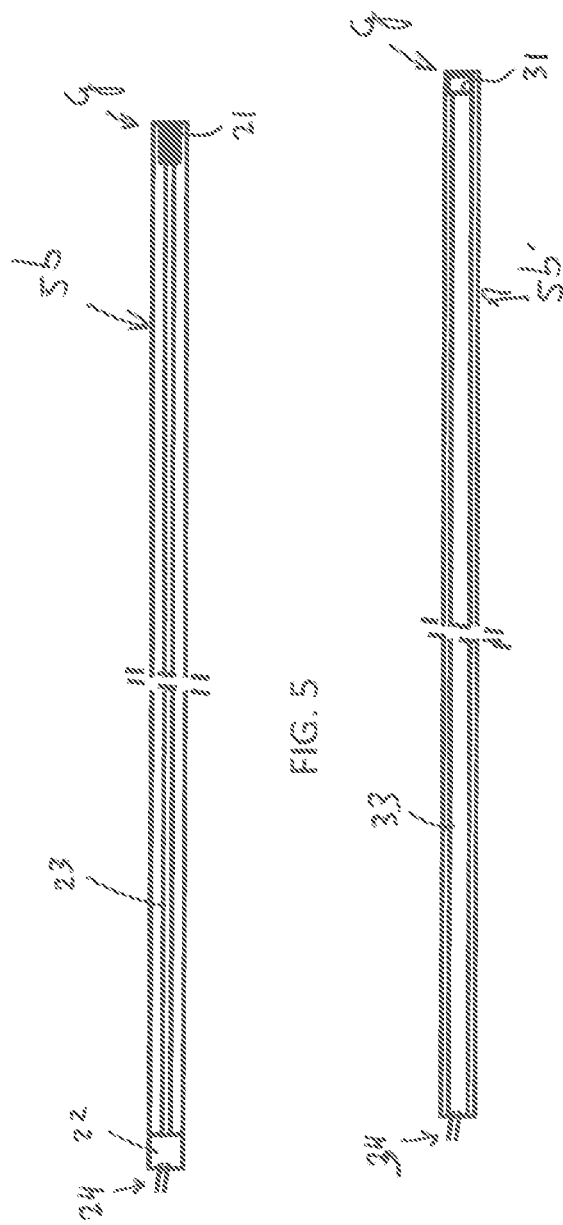

AFTERLOADING DEVICE, AND USE THEREOF

CROSS-REFERENCE TO RELATED APPLICATIONS

This patent application claims the benefit of priority under 35 U.S.C, §119 to The Netherlands Patent Application No. 2010838, filed on May 22, 2013, which is incorporated herein by reference in its entirety.

FIELD OF THE INVENTION

The invention relates to an afterloading device, and use thereof.

BACKGROUND OF THE INVENTION

An afterloading device as such (also known as "afterloader") is known, and currently marketed by the applicant. In the known afterloading device, usually, an Iridium-192 or Cobalt-60 radioactive source is used for effectuating brachytherapy. The radioactive source is stored in a radiation shielding vault inside a housing of the afterloading device. Particularly, the afterloading device may be a relatively compact system, including a mobile housing (i.e. mobile by a single person) that is e.g. supported on wheels.

The afterloading device includes dedicated driven cables for moving the radiation source to one or more treatment locations. The afterloading device generally defines a plurality of channels from which a cable with a source can be fed into external tubes/catheters, connected to those channels. The known afterloader device includes a selector for selecting a channel that is to be used (i.e. that is to deliver a source to a respective catheter connected to the channel). The external catheters may be coupled to, provided with or include an applicator (or probe), known as such to the skilled person, the applicator being located at a desired treatment location (e.g. near or inside tissue that is to be irradiated). Alternatively, one or more external catheters may be used as such, as dose applicator(s).

In the present radiation delivery practice, the radiation dose to be delivered to the patient is calculated beforehand by a suitable dose planning system. For example, the dose planning system may be arranged to calculate the radiation dose around a suitable target volume for a configuration, when a sole radioactive source is to be positioned along a plurality of dose delivery channels (for example, catheters). In this case, the total dose delivered by such displaceable radioactive source will result from a convolution of the individual dose deliveries for each dwell position of the source inside the catheters.

The dose planning system is thus used for optimizing the number of the dwell positions of the radioactive source and the corresponding dwell times, so that the convoluted total delivered dosed corresponds to the dose shape and value, prescribed by the doctor/user.

The output of the dose planning system is a number of source dwell positions and dwell times. These data may be automatically loaded into the afterloading device for implementing the actual treatment.

Accordingly, it is of paramount importance that the actual position of the radioactive source corresponds to the prescribed position as calculated by the dose planning system. In order to verify the radiotherapy treatment in-vivo dosimetry is desired.

WO 2008/009917, incorporated by reference in its entirety in the present application, discloses a brachytherapy system, having an in-vivo dose detector, wherein the detector is insertable into and movable through a catheter, and comprises a sensor operable to detect radiation from a source used to irradiate a tissue to be treated in the course of an HDR brachytherapy treatment. The known dose detector comprises a diode sensor that is operable to generate an electronic signal which is fed to an electrometer or other voltage or charge measuring device external to the patient. In the known system the readings from the radiation detector are controlled by the timer which is switched on once it is assumed that the radiation source has reached its dwell position. Radiation emitted by the source in the dwell position is detected in real time and both the detector reading and the integrated dose for the treatment procedure may be logged in real time. The thus obtained radiation dose may be compared with the planned dose for that position and/or the integral dose. Should either of the parameters show a substantial discrepancy with the planned parameters, the treatment is aborted.

It is a disadvantage of the system of WO 2008/009917 that the installing of the radiation detector, requires feeding the detector into the one of the catheters and subsequently connecting the detector to an electrometer, which is cumbersome and takes-up a lot of time, therefore lengthening the overall patient treatment process. Further, the known system assumes that the radiation delivery source is accurately positioned at the prescribed dwell position. However, in practice minor or even substantial discrepancies may occur, for example either due to change in the treatment geometry (catheter displacement inside the patient), or due to an improper positioning of the source, leading to significant deviations in actual treatment doses.

DESCRIPTION OF THE INVENTION

It is an object of the invention to provide an improved, efficient system and method for brachytherapy. An object is a system wherein in-vivo dosimetry is carried out with high accuracy and improved efficiency. It is a still further object of the invention to provide the afterloading device comprising a build-in in-vivo dosimetry system, wherein the build-in in-vivo dosimetry system enables effectuating system consistency checks, such as checks regarding correctness of the dose delivery geometry and configuration. It is a still further object of the invention to provide an afterloading device with a build-in in-vivo dosimetry system having an improved data collection circuit.

To this end an afterloading device according to an aspect of the invention comprises a first elongated flexible transport element, arranged to maneuver a radiation source between a storage position inside the afterloading device and a treatment position outside the afterloading device, the afterloading device further comprising a second elongated flexible transport element, having at least one transducer, the second transport element being arranged to move the at least one transducer between at least a first transducer position and a second transducer position.

For example, according to an embodiment, the afterloading device may comprise a displaceable radioactive source mounted on a first driven wire arranged to maneuver the source between a storage position inside the afterloading device and a treatment position outside the afterloading device, the afterloading device further comprises a radiation detector arranged for detecting radiation emitted by the radioactive source in the treatment position, wherein the radiation detector is mounted on a second driven wire, or driven cable, arranged for on demand maneuvering the radiation detector to a pre-known position outside the afterloading device.

A basic idea behind the invention is based on the insight of integrating a sensor or sensor part (i.e. transducer), for example a radiation detector or a spatial position detector, with a mechanical drive of the afterloading device (for example with a driven wire or driven cable). This provides numerous advantages as will be clear from the following. The afterloading device can operate efficiently and accurately. Particularly in the case the transducer is a source radiation transducer, an independent check of the source position and delivered dose outside the afterloading device may be enabled, utilizing the afterloader device as such for positioning the transducer towards one or more source monitoring locations. A treatment can be verified with minimal user interactions.

A positioning or repositioning of a said transducer can be carried out safely in case the radiation source has been driven out of the afterloading device, by the same afterloading device. Presence of an operator to position/reposition a transducer (i.e. close to the patient under treatment) is avoided.

In particular, according to an embodiment, the second driven elongated element may be arranged to position the transducer (e.g. radiation dose detector, sensor) for controlling each dwell position of the radiation source. In this way, transducer driving mechanics and radioactive source driving mechanics may operate independently, and any discrepancy between the reading of a transducer related radiation detector with an expected value shall point on the error (or mismatch) in the dose delivery configuration. It will be appreciated that once the radiation source is maneuvered inside one catheter, this catheter will not be used by the second elongated element (wire/cable) that includes the transducer (as long as the radiation source is inside that catheter). In such a case, in order to check the dwell position of the source and the delivered dose, the transducer can be positioned inside another catheter, e.g. at a position corresponding to the dwell position of the source.

According to an embodiment, the second transport element of the afterloading device is arranged to move the at least one transducer to a storage position inside the afterloading device, providing a compact configuration, advantageous e.g. for storage and/or transport of the afterloading device.

According to an embodiment, the second transport element of the afterloading device is arranged to move the at least one transducer to a detection position remote from the afterloading device, particularly for on demand maneuvering the transducer to a pre-known position outside the afterloading device. According to an embodiment, the remote detection position can be a position near a said treatment position of the radiation source, for example a detection position within 10 cm of the treatment position.

According to an embodiment, the afterloading device includes a plurality of exit openings for feeding each of the transport elements from positions stored in the afterloading device out of the afterloading device, the afterloading device preferably also including a selector mechanism that is configured to select which driven transport element is to pass which exit opening.

According to an embodiment, the afterloading device includes a communication device, wherein the second transport element is configured for transmitting information between the at least one transducer and the communication device of the afterloading device, for example for transmitting a transducer signal to the communication device. Alternatively or in addition, the second transport element can be configured for transmitting electric power between the at least one transducer and another part of the afterloading device.

The communication device can be configured in various ways as will be appreciated by the skilled person, and is preferably configured to send data (e.g. data received from the transducer or relating to a transducer signal of the transducer) to a afterloader device control system. The communication device may for example be at least partly integrated with a drive system for driving the second transport element. The communication device may be configured to communicate using wireless and/or wired communication links, as will be appreciated by the skilled person. For example, according to a non-limiting embodiment, the communication device and the second transport element may be configured to wirelessly transfer signals there-between, for example via induction or optically.

It is found that by using wireless data transfer a strict galvanic isolation is reached between electronic devices used for operation of the afterloading device and electronic devices used for implementing in-vivo dosimetry. This aspect is important for patient safety.

According to an embodiment, the second driven transport element is configured to transmit an optical signal to and/or from the at least one transducer. Also, according to an embodiment, the second driven transport element is configured to transmit an electrical signal to and/or from the at least one transducer. In case of transmission of electric signals, an advantageous embodiment provides that the second driven transport element comprises an electrically conducting coax cable, and preferably a triax cable. In particular, when a triaxial cable is used, the signal to noise ratio for the current measurements is improved.

Preferably, the diameter of the second driven transport element does not exceed 2 mm, particularly 1 mm. The same holds for the/each transducer of that element, and also for the first elongated driven transport element and radiation source. This technical measure is based on the insight that the sub-millimeter diameter is suitable to use 5F or 6F catheters (these catheters are usually used for applicators in brachytherapy) for receiving the elongated transport elements.

According to an embodiment, the second driven transport element can be controllable to be used as an afterloader check-wire. Afterloader check-wires, or dummy wires, as known and are usually applied for checking a route and/or integrity of a catheter before radiation treatment commences. To that aim, the check-wires are not provided with a radiation source. The second flexible transport element, carrying the at least one transducer, is also preferably not provided with a radiation source, making that element well suited for dummy wire operation. In other words, the functionality of the check-wire may be broadened as it may have two integrated functions, first, to check the geometry and consistency of a connection to the catheters and, secondly, to maneuver the transducer (e.g. radiation dose detector) to a suitable pre-determined position for carrying out in-vivo dosimetry.

According to an embodiment, the afterloading device further comprises an encoding device for measuring and/or controlling the displacement of the second driven transport element, and preferably also including an encoding device for measuring and/or controlling the displacement of the first driven transport element.

According to an embodiment, the afterloading device includes a revolving drum for driving the second driven cable. For example, the drum may comprise at least part of a said communication device.

According to a further embodiment, providing electric power to a said transducer of a second transport element, or to a said communication device, is achieved by electromagnetic induction. To that aim, a said drum may include a first inductor, wherein the transducer or a said communication device is electrically coupled to the first inductor to receive the electrical power. Also, a stationary part (e.g. a motor housing or another stationary part) of the afterloader device may include a second inductor, wherein the first and second inductor are arranged to cooperate, utilizing induction, to transmit electromagnetic energy/power there-between.

According to an embodiment, the transducer may be configured to convert at least part of incoming radiation into a transducer signal, for example to detect radiation emitted by the radiation source. In one further embodiment, the transducer is a diode, for example a PIN diode. Also, for example, the transducer may be a scintillator.

A diode can be used for the radiation detector. It will be appreciated that it may be sufficient to use a single dose meter for carrying out suitable in-vivo measurements. However, for circumstances when an additional reference is needed, such as for determination of the source position in 3D, an additional (external) dose detector may be used. This additional (external) dose detector may be a diode or a MOSFET detector, for example.

According to yet a further embodiment, the transducer is configured to measure the temperature, particularly its own temperature. This can be realized by using a semiconductor as a temperature sensor, for example a diode.

In a further advantageous embodiment, a said transducer of the second transport element is configured to convert an electromagnetic (EM) signal or EM field into another signal, for example into an electric signal. Also, or in addition, for example, the transducer may be a tracking sensor or probe, e.g. a spatial position detector.

Electromagnetic tracking sensors/probes are known as such, see for example the Aurora® Electromagnetic Measurement System of NDI, see also EP1272862B1. It follows that the transducer may be e.g. coil, configured to be located inside a volume e.g., a body of a medical patient via e.g. a catheter. A respective tracking system may include a plurality of external field sources, e.g. small induction coils, which are located outside of the volume. Other embodiments may place the field sources around the volume in which the tracking probe is located. In an example, during probe tracking, magnetic fields from the sources induce electromotive forces (EMFs) in the internal sensor coil of the probe. The EMFs are measured by an electronics module that connects to the probe.

According to an aspect of the present invention, a said second elongated transport element can be provided or may include a said tracking probe, providing efficient tracking capabilities to the afterloading device. In that case, preferably, the second elongated transport element is configured to transmit an electric probe signal of the tracking probe to a said communication device of the afterloading device. In that case, the communication device can be part of a tracking signal processing system, or communicate with such a system. For example, a said probe signal may be generated by a tracking coil transducer, being located in and/or moving through a catheter that is located in the EM field, the coil picking up the EM field to generate the probe signal.

Also according to an aspect of the present invention, in a further embodiment, is to use several main applicator independence measurements reference points in or near a patient, for example three or more points, for the spatial position measurements of the dose applicator(s).

In a further embodiment of the afterloading device it is arranged to interact with a dose planning system for acquiring the source treatment position. It is found to be particularly advantageous to enable electronic data transfer between the dose planning system used for calculating the dwell positions of the source and the corresponding partial delivered dose and the afterloading device. In this way it is ensured that no human errors occur when defining the pre-known position for the radiation source.

According to yet a further embodiment, the afterloading device is configured to control the temperature of a said transducer of a said second transport element. Particularly, the afterloading device may be configured to thermally condition the transducer, e.g. when the transducer is in a storage position, or at least when the transducer is inside a housing of the afterloading device.

Further aspects of the invention provide the use of an afterloading device according to the invention, including: driving the second elongated flexible transport element, thereby moving the at least one transducer between the first transducer position and the second transducer position. Thus, the above-mentioned advantages can be achieved.

In case the transducer is used to detect radiation emitted by the radiation source, a further embodiment includes calibrating the transducer utilizing radiation emanating from the radiation source of the first driven transport element. Such a calibrating particularly includes:

mutually positioning the transducer and the radiation source at at least one measuring distance and determining a transducer signal resulting from the transducer receiving radiation from the source at that measuring distance;

storing and/or processing the determined transducer signal to provide transducer calibration data.

Also, in a further embodiment, during the calibrating, the transducer and the radiation source may both be located within a housing of the afterloading device, so that the calibration can be carried out swiftly and safely. Besides, optionally, such a calibration can be carried out when the transducer and the radiation source are both located outside a housing of the afterloading device. To that aim, a housing of the afterloading device may optionally be temporarily provided with an external receiving device (for example a box) for receiving the transducer and the radiation source, wherein the receiving device may e.g. be configured to hold the transducer and the radiation source at one or more predetermined distances from each other.

A use of the afterloading device can include that the second elongated flexible transport element is driven to maneuver the transducer to a predetermined transducer position, external to the afterloading device, wherein the first elongated flexible transport element is driven to maneuver the radiation source towards a predetermined source position, external to the afterloading device, wherein the transducer is used in verifying and/or controlling the positioning of the radiation source.

Further, a use of the afterloading device can include detecting or monitoring the position of the transducer utilizing a dedicated monitoring system, for example an imaging system. The imaging system may e.g. be an MRI (magnetic resonance imaging) system or a different type of system A highly advantageous use involves application of the afterloading device for brachytherapy.

According to another independent aspect of the invention, there is provided an afterloading device for effectuating a brachytherapy treatment, comprising a first elongated flexible transport element, arranged to maneuver a radiation source between a storage position inside the afterloading device and a treatment position outside the afterloading device, wherein the first transport element is also arranged to move at least one transducer between a first transducer position and a second transducer position. For example, the first elongated flexible transport element can be provided with both the source and the transducer, for example at a relatively short distance from each other. The transducer of the first elongated flexible transport element may be a source radiation detector, of for example a spatial position detector, or a different transducer.

These and other aspects of the invention will be discussed in more detail with reference to Figures, wherein like reference numerals represent like elements. It will be appreciated that the figures are presented for illustration purposes only and may not be used for limiting the scope of the appended claims.

BRIEF DESCRIPTION OF THE DRAWINGS

FIG. 5 schematically depicts a first example of a transport element of the embodiment of FIG. 1;

FIG. 6 schematically depicts a second example of a transport element of the embodiment of FIG. 1.

FIGS. 1-2 show an example of an afterloading device 1 for effectuating a brachytherapy treatment. In the example, the afterloading device (or "afterloader") can be part of a brachytherapy system that further includes e.g. a brachytherapy control or computer device C, as well as a plurality of catheters 8a, 8b, 8c (see also FIG. 3). The catheters, know per se, are for inserting one or more radiation sources S into a region of tissue T of a patient that is to be treated. FIG. 3 depicts distal sections of inserted catheters 8a, 8b, 8c, a said radiation source S, a said patient's tissue T to be treated. Dashed rectangle P schematically depicts a section of the patient that includes the tissue T. Two of the catheters 8a, 8b are also depicted in FIG. 2. The catheters 8a, 8b, 8c as such can be configured in various ways, for example having a diameter of 1.2 mm or another diameter, as will be appreciated by the skilled person.

Figure 2:
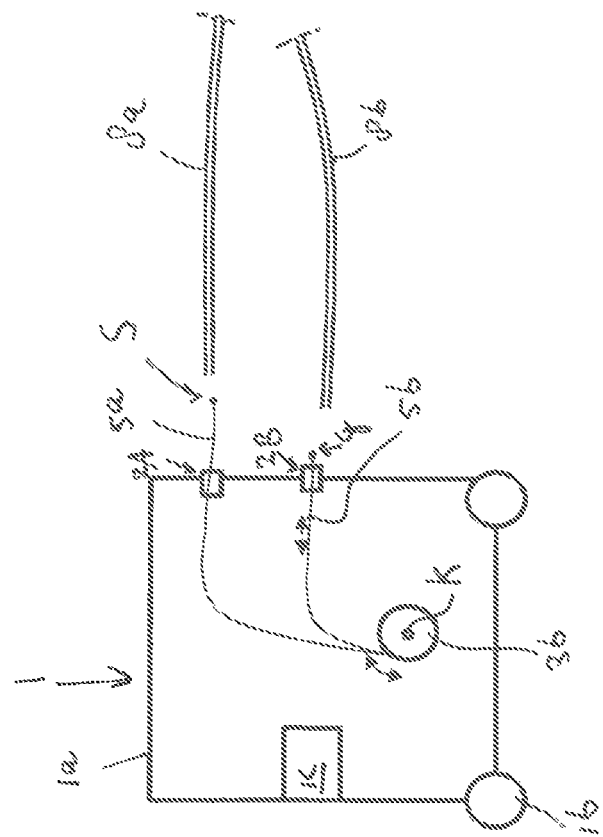
FIG. 2 schematically shows cross-section over line II-II of FIG. 1.
Figure 1:
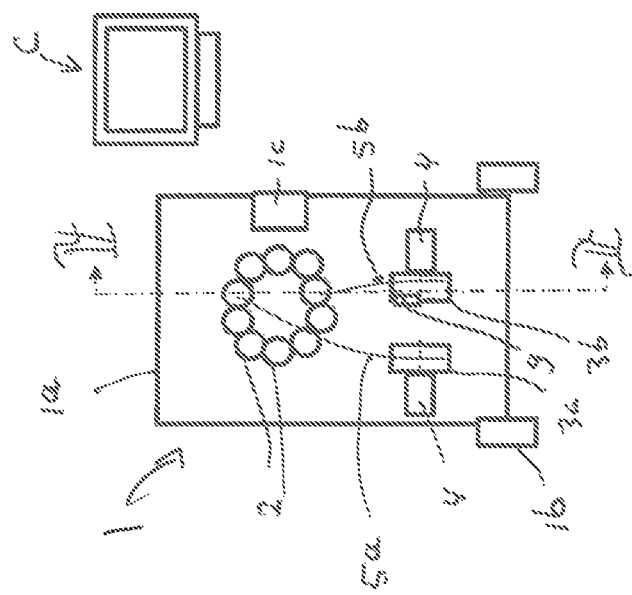
FIG. 1 schematically shows a partially opened front view of a non-limited embodiment of the invention.

For example, the afterloader 1 is operable to drive a one or more radioactive sources (one being shown as source S) into and out of a plurality (e.g. a bundle) of catheters 8a, 8b, 8c that have been inserted into the region of tissue T of the patient that is to be treated. As will be clear to the skilled person, prior to the brachytherapy treatment, the position of the catheters 8a, 8b, 8c with respect to the tissue T can be verified by any one of a number of imaging systems, for example by means of an ultrasound or x-ray imaging system. Each source S, which is typically of Iridium-192 or Cobalt-60, is of such a size that it can be advanced by the afterloader through the source catheter 8a.

The present afterloading device 1 is a mobile device, including a housing 1a that is supported on a number of wheels 1b, particularly such that the housing can be manually moved to desired treatment locations (e.g. near a patient support structure) by a single person.

The afterloading device 1 particularly comprises at least a first elongated flexible transport element 5a, arranged to maneuver a respective radiation source S between a storage position inside the afterloading device (i.e. inside a housing 1a of the device 1) and a treatment position (see FIG. 3) outside the afterloading device 1. The source S is connected to a distal end of the first transport element). As is mentioned before, preferably, the afterloading device 1 includes a radiation shielding vault (not shown) inside the housing 1a, for providing a safe storage location for each source S.

The first elongated flexible transport element 5a may be configured in various ways, and may e.g. be a flexible wire that can be pushed through a said catheter 8a by the afterloading device 1.

Figure 4:
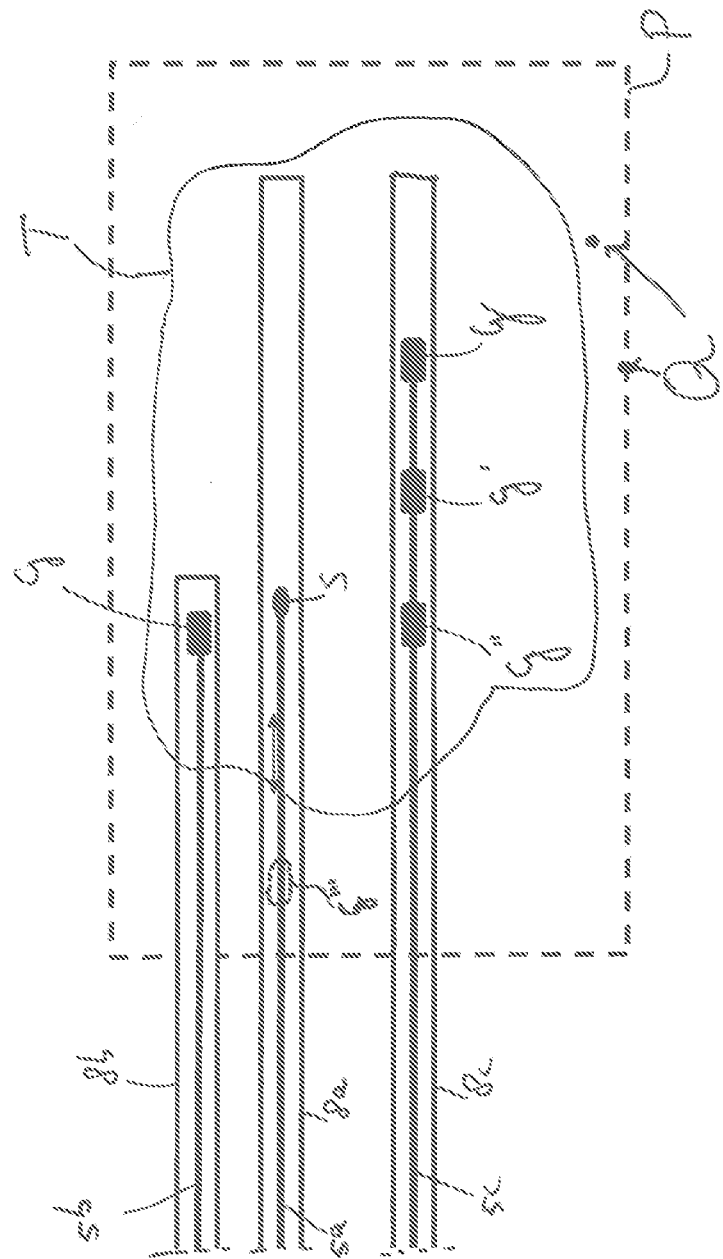
FIG. 4 schematically part of a further embodiment during operation.

The afterloading device 1 further comprises at least a second driven elongated flexible transport element 5b, 5c (see also FIG. 4). A highly advantageous embodiment of the second driven elongated flexible transport element 5b, 5c will be explained below.

The afterloading device includes drive mechanisms 3a, 3b, 4 for driving the transport elements 5a, 5b, 5c. Particularly, each drive mechanism may include a revolving drum 3a, 3b, driven by a respective motor 4, for unwinding and winding a respective elongated flexible transport element 5a, 5b. Rotation of a second drum 3b around an axis of rotation K and a respective displacement of the second transport element 5b is indicated by arrows in FIG. 2. The device 1 may include further drive mechanisms (not shown), including a revolving drum driven by a respective motor, for driving further transport elements (such as the third driven elongated transport element 5c shown in FIG. 4), as will be appreciated by the skilled person.

Preferably, the drive mechanisms 3a, 3b, 4 can be controlled with high precision, allowing for accurate displacements of the respective transport elements 5a, 5b. To that aim, preferably, the afterloading device 1 may comprise encoding devices for measuring and/or controlling the displacement of the each driven transport element 5a, 5b. Such encoding devices may be integrated in the drive mechanisms 3a, 3b, 4, as will be appreciated by the skilled person, and are known as such.

The afterloading device 1 may include a plurality of exit openings 2 for feeding each of the transport elements from positions stored in the afterloading device out of the afterloading device. The afterloading device 1 preferably also including a selector mechanism (not shown) that is configured to select which driven transport element is to pass which exit opening 2. As is indicated in FIG. 2. e.g. a first exit opening 2A may be selected during operation, for feeding a source transport element 5a out of the housing a of the device 1, into a respective first catheter 8a. Such a catheter 8a may be directly or indirectly connected to the device 1, as will be appreciated by the skilled person (an indirect connection e.g. being achieved by an intermediate transfer tube, known per se). A second exit opening 2B may be selected during operation, for feeding a second transport element 5b, into a respective second catheter 8b. Proximal ends of the catheters 8a, 8b (or respective transfer tubes) may e.g. be removably coupled to the afterloading device 1, at desired or selected exit ports 2, for example via operably locking means, as will be clear to the skilled person.

Figure 3:
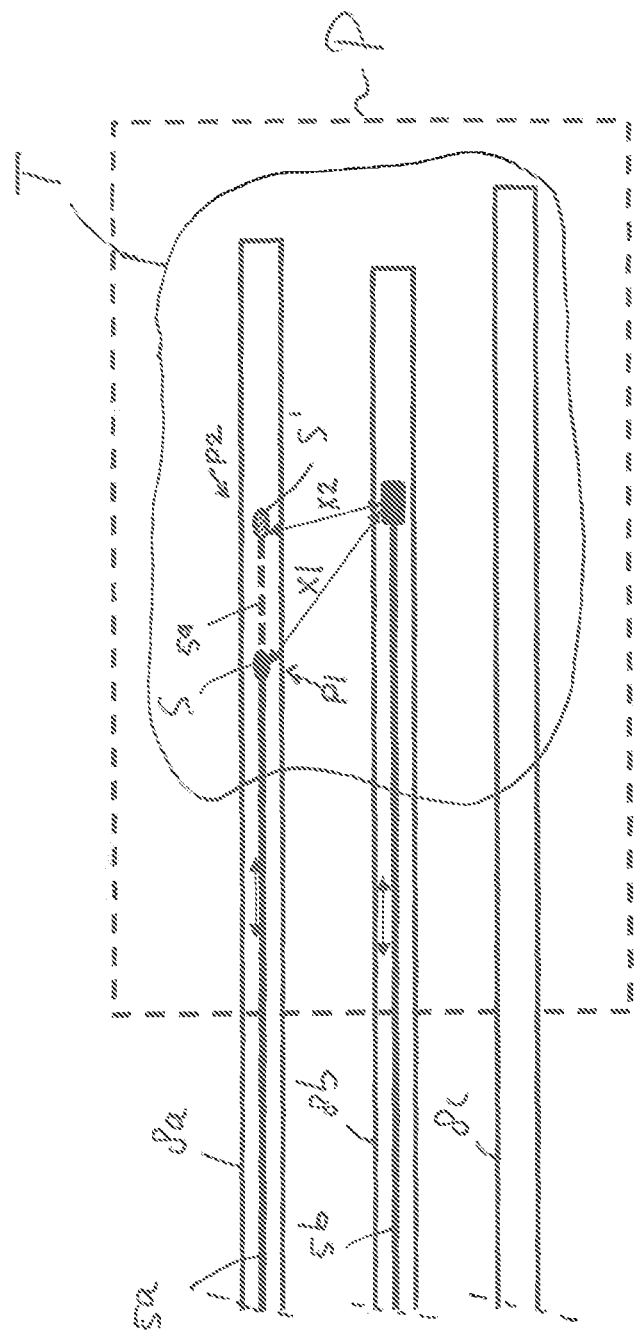
FIG. 3 schematically part of the embodiment of FIG. 1 during operation.

An external controller or computing resource C, for example a computer, may be provided for controlling the afterloading device 1. In the example, the afterloading device 1 may itself include a control unit 1c for locally controlling the drive mechanisms and a said selector mechanism, based on control signals received from controller C. Communication means (not shown) may be provided, for example wired or wireless communication lines, between the external controller C and the controller 1a of the afterloading device 1, for communicating control signals therebetween. The external controller C can be configured to control the afterloader 1. e.g. via the dedicated afterloader controller 1a, in accordance with a treatment plan that has been devised under the supervision of a physician to deliver an appropriate dose of radiation to the tissue that is to be treated by brachytherapy. The treatment plan consists e.g. for each source S that is to be inserted into the patient P, a list of dwell positions (longitudinal positions P1, P2 within a given catheter 8a to which the source is to be advanced) and a dwell time (a period of time for which the source S is stationary at each dwell position) for each of those dwell positions. Two such source positions P1, P2 are shown in FIG. 3, a crosshatched source S' depicting a second source position P2 after a further movement of the source S (from a first position P1) by a movement the respective drive element 5a (over section 5a3 through the first catheter 8a.

Advantageously, each second elongated flexible transport element 5b, 5c includes or is provided with at least one transducer G, the second transport element 5b being arranged to move the transducer G between a first transducer position and a second transducer position. A said transducer G may be located at various positions of the second transport element 5b, for example at or near a distal end of that element 5b (as in FIGS. 2, 3) or remote from the distal tip of that element 5c (see the second transducer G' and third transducer G" of the further transport element 5c in FIG. 4). Preferably, each second elongated flexible transport element 5b, 5c that includes or is provided with the at least one transducer G is not provided with a said radiation source S for effecting the radiation treatment of tissue T.

Alternatively, for example, the first elongated flexible transport element 5a may also include a transducer, e.g. at a relatively short distance behind the source S (i.e. remote from the distal tip of the flexible transport element 5a). This is schematically indicated by a transducer G'" in FIG. 4, shown with a dashed line.

Each second elongated flexible transport element 5b may be configured in various ways, and may e.g. be a flexible transport wire or flexible cable that can be pushed through a said catheter 8a by the afterloading device 1. According to a further embodiment, the diameter of the second driven transport element 5b does not exceed 2 mm, preferably 1 mm. The same holds for each transducer G of that element 5b.

According to a preferred embodiment, the afterloading device 1 can be arranged to move the at least one transducer G to a storage position inside the afterloading device (i.e. inside the housing 1a), by withdrawing the respective second elongated flexible transport element 5b into the housing 1a. Further, the afterloading device may be arranged to move the at least one transducer G, utilizing the respective driven transport element 5b, to a detection position remote from the afterloading device, particularly for on demand maneuvering the transducer G to a pre-known position outside the afterloading device 1. Such remote transducer positions are shown in FIGS. 3, 4. Particularly, during operation, the transducer G can be located near the tissue T that is to be treated, e.g. before the source S is moved into treatment position. For example, a said detection position may be a position near a said treatment position (dwell position) P1. P2 of the radiation source S, for example a detection position within 10 cm of the treatment position.

A said transducer G, G', G", G'" can be configured in various ways. According to a preferred embodiment, the transducer G, G', G", G'" is configured to convert at least part of incoming radiation into a transducer signal, for example to detect radiation emitted by the radiation source S. Also, according to a further embodiment, the transducer may includes a scintillator 21 (see FIG. 5). According to another embodiment (see FIG. 6), the transducer G may include a diode 31, for example a PIN diode (i.e. a diode including a stack of a p-doped, intrinsic and n-doped material). Also, for example, the transducer may be similar to the in vivo dose detector described in WO 2008/009917, or other known in-vivo dose detectors. Besides, as has been mentioned before, the transducer may be a spatial position detector, for example the said coil, particularly a EM field coil to be used as part of an EM tracking system (know as such).

Figure 7:
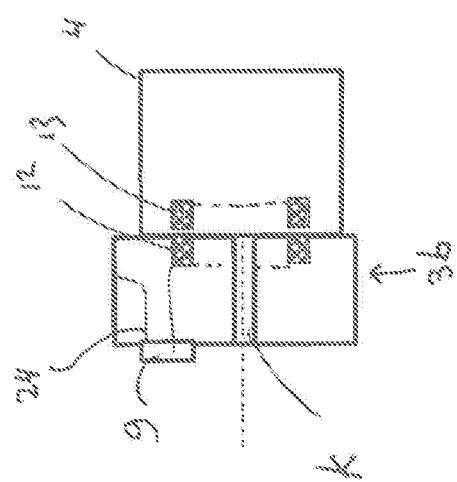
FIG. 7 shows a detail of the embodiment shown in FIG. 1.

The afterloading device 1 preferably includes a communication device 9. The second transport element 5b is preferably configured for transmitting information between the at least one transducer G and the communication device 9 of the afterloading device, for example for transmitting a transducer signal to the communication device 9. Communicative connection between the communication device 9 and the transport element 5b can be achieved in various ways, depending e.g. on the type of signal that is to be communicated. In the example, the drive mechanism of the second transport element 5b includes or is provided with a said communication device. A particularly example of such a configuration is shown in FIG. 7, described here-below.

The second transport element 5b may be configured for transmission of optical signals emanating from the transducer G. To that aim, the second transport element 5b may include at least one optical waveguide 23, for example one or more optical fibers, or a fibre optical cable, as is schematically depicted in FIG. 5. For example, the transducer G, such as scintillator 21, may be configured to convert incoming source radiation into an optical signal. In that case, the optical signal can be transmitted via the waveguide 23 to a proximal end of the second transport element 5b. In yet a further embodiment, the a proximal end of the second transport element 5b may include or be provided with a detector 22, e.g. a photo diode, for detecting the optical signal, wherein the detector 22 can be configured to generate or provide an electric detection signal at a detector output/terminal 24 upon detection of the optical signal.

Referring to FIG. 6, alternatively, e.g., the second transport element 5b may be configured for transmission of electrical signals to and/or from the transducer G, in case the transducer G is configured to generate or adjust an electrical signal upon receiving radiation from a radiation source S. In that case, the second transport element 5b may include at least one electrical signal conductor 33. For example, to that aim, the second transport element 5b may include or mainly consist of an electrically conducting coax-cable, or advantageously of a triax-cable (providing improved signal to noise ratio). An electric signal can be transmitted via the at least one electrical signal conductor 33 to a proximal end of the second transport element, for example to be communicated with a said communication device 9 via a respective output/terminal 34 that may be provided at a proximal end of the transport element 5b.

According to an example, the drive mechanism (e.g. the drum) may comprises at least part of the communication device 9. Referring to FIG. 7, a driven drum 3b of the afterloading device may carry or include a communication device 9, being in direct or indirect communicative contact with a said transducer G, e.g. via terminals or electric wiring 24 and a signal transmission line provided by a respective second driven element 5b (driven by the same drum 3b). In a further embodiment, the communication device 9 may be configured to process or filter signals, received from the respective second transport element 5b. The communication device 9 may be further configured to communicate with a said local control unit 1c and/or with a said brachytherapy control or computer device C, for example via wireless communication means. The communication device 9 may include a dedicated power source, for example a battery, for powering that device 9.

According to a further embodiment, signal transmission with communication device 9 and/or providing power to that device is achieved by electromagnetic induction. To that aim, the drum 3b may include a first inductor 12, e.g. a first coil 12 arranged concentrically with respect of the axis of rotation K, wherein the communication device 9 is electrically linked to the first inductor 12 for transmission of electric signals and/or power there-between. A nearby stationary part (e.g. a motor housing or another stationary part) may include a second inductor 13. e.g. a second coil 13 arranged concentrically with respect of the axis of rotation K. In an embodiment, the inductors 12, 13 cooperate, utilizing induction, to transmit electromagnetic energy (signals and/or power) there-between, for example to feed electric power to the communication device 9, and/or for transmitting communication signals between that device 9 and another part of the afterloader 1 (e.g. the controller 1c).

According to a further embodiment, the afterloading device is configured to use several position measurement points Q as reference points of the measurement points in the dose applicators. For example, use can be made of several main applicator independent measurements reference points Q in, on and/or or near a patient, for example three or more points, for the spatial position measurements of the dose applicator(s). Two of such reference points is shown in FIG. 4, at Q (one independent reference point being on the patient, and one point being inside the patient). Optionally, one or more of these reference points Q may be provided with its own a spatial position detector or marker, to be detected by a respective position detection system.

Use of the afterloader 1 may involve utilizing a said transducer G as a detector, e.g. to detect radiation. However, according to an embodiment, a said second driven transport element 5b, 5c may also be controllable to be used as an afterloader check-wire ('dummy wire'), for example to check catheter integrity with or without being active as a detector section, and when the source S is still located at a stored position in the afterloading device.

FIGS. 3, 4 show examples of use of the afterloading device 1. During operation, the second elongated flexible transport element 5b is simply driven by the respective drive mechanism 4, 5b of the afterloader, thereby moving the respective transducer G between a first transducer position and a second transducer position. For example, the transducer G may be moved from a stored position (i.e. stored within the housing of the afterloader), via an outlet port 2B and catheter 8b, to a position inside or near a tissue T that is to be irradiated (see FIG. 3). A selected second position may e.g. be monitored or verified, using a dedicated monitoring system, for example an imaging system (not shown), during or after the displacement of the transducer G. Besides, a said second position of the transducer G may be controlled using measurement results of a said encoding device, measuring and/or controlling the displacement of the second driven transport element 5b.

Next, one or more sources (one S, in this example) may be transferred by the afterloading device 1 towards selected treatment positions P1, P2, via respective catheters. In case of a radiation transducer G, the installed transducer G can then be used to detect radiation emitted by the radiation source S, for example to verify the location of the source, to verify or monitor a dose that is delivered by the source, particularly to provide in-vivo dosimetry. Signals relating to the detection of the radiation can be transmitted simply via the second driven element 5b to the afterloading device 1, particularly to the said communication device 9.

Furthermore, the transducer G may e.g. be used to determine or estimate a first distance X1 and a subsequent second distance X2 between transducer G and source. Preferably, such a determination or estimation is carried out automatically, e.g. by a controller C, and can be based on predetermined transducer calibration data (the data e.g. including a predetermined relation between the distance between the particular radiation source S and the transducer G on one hand and a transducer signal on the other hand).

According to an embodiment, movement of the radiation source S through a catheter 8a may be carried out simultaneously with moving a transducer G through a catheter, both movements being induced by the same afterloading device 1. For example, a transducer G may be moved in concert with the source S.

Also, according to an embodiment, when the radiation source S is located at a predetermined treatment location P1, P2 in a source catheter 5a, a transducer G may be moved through a catheter 8b by the afterloading device 1, for example towards a position of highest radiation, or to find such a position.

FIG. 3 further shows a third catheter 8c, being inserted near the source catheter 5a and second catheter 5b. The third catheter 8c may be used to receive the source transport element 5a as well (i.e. after the source has been retracted from the first catheter 8a), or for receiving a further elongated driven element carrying one or more further transducers G, G'; G". The latter option is schematically depicted in FIG. 4, wherein a further elongated driven element 5c, including an array of transducers G, G', G" has been maneuvered by the afterloading device 1 to a position near the tissue T to be treated. In this embodiment, the further driven element 5c is preferably configured to independently transmit signals relating to each of the array of transducers G, G', G" to a proximal end of the driven element 5c, to be further processed by a respective communication device. The application of at least two driven elements 5b, 5c having respective transducers G, via at least two respective catheters 8b, 8c, allows for a more accurate monitoring and control of the radiation treatment.

The present invention allows for reduction of afterloader handing errors. For example, a serious handling error may involve an operator connecting the wrong catheter to certain afterloader outlet ports 2, e.g. by mixing up catheters. The second transport element, having the at least one transducer, can serve as an early warning device, providing source induced transducer signals that may deviate from expected values in case of a handling error. In that case, the afterloading device 1, or the system including the device 1, may be configured to automatically abort a treatment, and to withdraw the source S.

According to a further advantageous embodiment, the afterloading device 1, or the system 1, C, may be configured to calibrate the transducer G. The afterloading device 1, or the system 1, C, may include a memory for storing calibration data, resulting from such a calibration.

The calibration can include: calibrating the transducer G utilizing radiation emanating from the radiation source S of the first driven transport element 5a. The calibrating particularly includes:

mutually positioning the transducer G and the radiation source S at at least one (mutual) measuring distance and determining a transducer signal resulting from the transducer G receiving radiation from the source at that measuring distance;

storing and/or processing each determined transducer signal to provide transducer calibration data.

The calibration may be based upon predetermined information regarding the source S as such, for example accurate dosimeter measurement results that have been provided by an external dosimeter (not shown), and/or a source certificate (known as such) indicating the source strength.

The positioning of the transducer G and the radiation source S at at least one (mutual) measuring distance (preferably a plurality of measuring distances) can be carried out automatically, by the afterloading device 1. It may include a scanning movement between the transducer G and the radiation source S (e.g. scanning the transducer G along the source S, or scanning the source along the transducer G). Also, the calibration steps can be carried out in automated manner, e.g. under control of the afterloader controller 1c and/or system controller C. The transducer G and the radiation source S may be e.g. both located within a housing 1a of the afterloading device during the calibrating, or for example at or near the outlet openings/ports 2 of the afterloading device 1.

In the foregoing specification, the invention has been described with reference to specific examples of embodiments of the invention. It will, however, be evident that various modifications and changes may be made therein without departing from the broader spirit and scope of the invention as set forth in the appended claims.

In the claims, any reference signs placed between parentheses shall not be construed as limiting the claim. The word 'comprising' does not exclude the presence of other features or steps then those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to advantage.

For example, according to a further advantageous embodiment, the afterloading device 1 is configured to control a temperature of a said transducer G of a said second transport element. Particularly, the afterloading device 1 may be configured to thermally condition the transducer G when it is in a storage position, or at least when the transducer is inside a housing of the afterloading device 1. To that aim, as an example, the afterloading device 1 may include a temperature conditioner or a heating means, e.g. an electrical heater, for heating the transducer G. More particularly, the temperature of the transducer G may be conditioned by the device 1 to a predetermined operating temperature, e.g. to a patient body temperature or a temperature of tissue that is to be treated, e.g. a temperature of about 37° C. to about 38° C. A said transducer temperature conditioner may be installed e.g. at a storage position of the transducer G. The thermal conditioning of the transducer G is particularly advantageous in the case that the transducer operation as such is temperature sensitive (i.e.: in case thermal fluctuations lead to differences in transducing by the transduce G). A said thermal conditional may e.g. be carried out at least before or at the start of a brachytherapy treatment, and/or before an optional transducer calibration process.

Also, for example, an afterloading device may comprise a first elongated flexible transport element, arranged to maneuver a radiation source between a storage position inside the afterloading device and a treatment position outside the afterloading device, the afterloading device e.g. further comprising a second elongated flexible transport element that does not have the at least one transducer. For example, as is mentioned before, advantageously, the first transport element can be arranged to move at least one transducer G''' between a first transducer position and a second transducer position (see FIG. 4).

The invention claimed is:

1. A system for performing a radiotherapy-related procedure, the system comprising:
   an afterloader device for delivering radiation treatment and configured to position at least one transducer toward one or more source monitoring locations;
   a first element configured to maneuver a radiation source from a source storage position located inside of the afterloader device to a first source position located outside of the afterloader device and within a delivery channel positioned within a body of a patient;
   a second element including the at least one transducer, the at least one transducer being configured to detect a parameter indicative of a radiation source position and generate a transducer signal, and wherein the second element is configured to move the at least one transducer from a first transducer position to a second transducer position at which the transducer detects the parameter indicative of the radiation source position, wherein the transducer is configured to communicate the transducer signal to the afterloader device; and
   a controller that determines a position of the radiation source along a length of the delivery channel based on the transducer signal.

2. The system of claim 1, wherein the second element is further arranged to move the at least one transducer to a transducer storage location inside of the afterloader device.

3. The system of claim 1,
   wherein the afterloader device further includes a plurality of openings and a plurality of transducer storage locations inside of the afterloader device, and
   wherein the system includes a plurality of second elements, where each of the plurality of openings extends from a respective transducer storage location to communicate with a region outside of the afterloader device and is dimensioned to receive a corresponding second element therethrough, and wherein the afterloader device is configured to select a particular one of the plurality of second elements to pass through a particular one of the plurality of openings.

4. The system of claim 1, wherein the afterloader device includes a communication device configured to receive the transducer signal, and wherein the second element includes a communication cable, such that the transducer signal is communicable from the transducer to the communication device via the second element.

5. The system of claim 4, wherein the parameter indicative of a radiation source position is a radiation parameter, the transducer comprises a radiation detector, and the parameter indicative of a radiation source position is determined based on an amount of radiation emitted from the radiation source that is detected by the radiation detector.

6. The system of claim 5, wherein the radiation detector includes at least one of a scintillator or a diode.

7. The system of claim 4, wherein the detected parameter is a distance parameter and the transducer comprises a spatial position detector configured to detect a position of the radiation source based on an electromagnetic signal detected by the spatial position detector.

8. The system of claim 7, wherein the spatial position detector includes an electromagnetic coil.

9. The system of claim 1, wherein the afterloader device includes a communication device configured to receive the transducer signal, and wherein the transducer is configured to wirelessly transmit the transducer signal to the communication device.

10. The system according to claim 1, wherein a diameter of the second element is less than approximately 2 millimeters.

11. The system according to claim 1, wherein the detected parameter includes temperature.

12. A method of performing a radiotherapy-related procedure, comprising:
maneuvering a radiation source from a source storage position located inside of an afterloader device to a first source position located outside of the afterloader device via a first element;
moving a transducer from a first transducer position to a second transducer position via the afterloader and a second element;
detecting, with the transducer, a parameter indicative of a position of the radiation source and generating a transducer signal, wherein at least one of the transducer or the radiation source is moved to detect the parameter indicative of the position of the radiation source; and
determining, using a controller, and based on the transducer signal, a position of the radiation source.

13. The method according to claim 12, further comprising moving the transducer to a third transducer position.

14. The method according to claim 12, wherein the first transducer position is a storage location within the afterloader device.

15. The method according to claim 12, wherein the second transducer position is within approximately 10 centimeters from a source position.

16. The method according to claim 12, further comprising:
positioning the transducer and the radiation source at a predetermined measuring distance away from each other;
detecting, with the transducer, a portion of radiation emitted from the radiation source at the measuring distance and generating a transducer signal; and
calibrating the transducer based on the generated transducer signal.

17. The method according to claim 16, wherein the transducer and the radiation source are both located within the afterloader device during the calibrating.

18. The method according to claim 12, further comprising verifying a positioning of the radiation source based at least in part on the generated transducer signal.

19. The method according to claim 12, further comprising monitoring a position of the transducer using an imaging system.

20. A method of performing a radiotherapy-related procedure, comprising:
maneuvering a radiation source from a source storage position located inside of an afterloader device to a first source position located outside of the afterloader device via a first element;
moving a transducer from a first transducer position to a second transducer position via the afterloader and a second element;
detecting, with the transducer, a first parameter indicative of a first position of the radiation source and generating a first transducer signal;
maneuvering the radiation source to a second source position located outside of the afterloader device via the first element;
detecting, with the transducer, a second parameter indicative of a second position of the radiation source and generating a second transducer signal; and
determining, using a controller, and based on the first and the second transducer signals, a first position and a second position of the radiation source.

* * * * *